United States Patent [19]

Kappas et al.

[11] Patent Number: 4,782,049

[45] Date of Patent: Nov. 1, 1988

[54] TIN PROTOPORPHYRIN AND TIN MESOPORPHYRIN IN THE TREATMENT OF PSORIASIS

[75] Inventors: Attallah Kappas; George S. Drummond, both of New York, N.Y.; Lennart Emtestam, Huddinge, Sweden

[73] Assignee: The Rockefeller University, New York, N.Y.

[21] Appl. No.: 125,011

[22] Filed: Dec. 2, 1987

Related U.S. Application Data

[63] Continuation-in-part of Ser. No. 938,822, Dec. 8, 1986, abandoned.

[51] Int. Cl.⁴ ............................................ A61K 31/555

[52] U.S. Cl. ..................................... 514/185; 514/863
[58] Field of Search ............................. 514/18 T, 863

[56] References Cited

U.S. PATENT DOCUMENTS 4,454,152  6/1984  Barry et al. ......................... 824/283
4,657,902  4/1987  Kappas et al. ...................... 514/185

Primary Examiner—Leonard Schenkman
Attorney, Agent, or Firm—Wyatt, Gerber, Burke and Badie

[57] ABSTRACT

Use of tin protoporphyrin and tin mesoporphyrin together with ultraviolet light in the treatment of psoriasis.

4 Claims, No Drawings

TIN PROTOPORPHYRIN AND TIN MESOPORPHYRIN IN THE TREATMENT OF PSORIASIS

RELATED APPLICATION

This application is a continuation-in-part of copending application Ser. No. 938,822 filed Dec. 8, 1986 now abandoned.

BACKGROUND OF THE INVENTION

This invention relates to methods of treating humans afflicted with psoriasis by treatment with an antipsoriatic amount of tin protoporphyrin (SnPP) or tin mesoporphyrin (SnMP).

Both SnPP and SnMP are known compounds. Their utility in the treatment of hyperbilirubinemia has been described by Drummond and Kappas. The utility of SnPP for this purpose is described in *Proc. Nat. Acad. Sci. USA* 78 6466–6470 (1981). The use of SnMP is described in commonly owned copending patent application Ser. No.: 715,515 filed Mar. 25, 1985 now U.S. Pat. No. 4,657,902.

Clinically, psoriasis vulgaris is characterized by erythematous, scaling plaques that often begin in the extensor aspects of the body. It may be extremely widespread, with occasional total skin involvement. It is frequently distressing to the patient and occasionally life threatening.

Other clinical types of psoriasis include generalized pustular psoriasis, localized pustular psoriasis of palms and soles, and exfoliative or erythrodermic psoriasis.

Histologically, psoriasis is characterized by acanthosis (thickened epidermis) and parakeratosis (nucleated cells in stratum corneum) and has been described as showing benign hyperplasia. The dermal blood vessels are abnormally tortuous and dilated, and lymphocytic infiltration is frequently seen in the dermis and occasionally in the epidermis.

It is not known whether the available antipsoriatic drugs act to slow cell proliferation primarily or to normalize keratinization. Some of the effective therapies appear to act as antiproliferative agents, and either reduce rates of epidermal KNA synthesis and/or mitosis, or both. For example, topical corticosteroids, anthralin, methotrexate, topical 5-fluorouracil, psoralen plus longwave ultraviolet light inhibit epidermal DNA synthesis and/or mitotic rate. Retinoids, however, may act primarily partially to correct the abnormal differentiation seen in psoriasis.

Many treatments involving a wide variety of therapeutic agents have been used in attempts to ameliorate psoriasis. These have included the use of topical and systemic steroids; various coal tar preparations, often in association with untraviolet light treatments, trihydroxyanthracene (Dithranol), and methotrexate. More recently, psoralen which is 7H-furo[3,2-g][1] benzopyran-7-one in associated with ultraviolet light has been widely investigated as a method of treatment. The method is known as PUVA.

Despite extensive and strenous efforts no completely satisfactory method of treating human psoriasis has yet been devised.

THE INVENTION

It has now been discovered that SnPP and SnMP have antipsoriatic activity when administered to humans. The active agents may be administered parenterally in solution or suspension, or topically in a suitable cream or ointment. The patient is exposed to ultraviolet light as an integral part of the treatment.

For parenteral administration any of a wide variety of pharmaceutically acceptable carriers currently in use for the preparation of therapeutically useful parenteral compositions may be employed. These include, for example, vegetable and mineral oils such as sesame oil, cottonseed oil and various mineral oil fractions. Aqueous media made isotonic by the addition of sodium chloride, glucose or other standard solutes are presently preferred. The compositions may be buffered to maintain a fixed pH, normally between 7 and 8. The preferred pH is from 7.4 to 7.5.

Typically an isotonic solution can be prepared by dissolving the selected amount of SnPP or SnMP in 0.2N aqueous sodium hydroxide solution, adjusting to the selected pH with 1N hydrochloric acid, and making up to volume with 0.9% aqueous sodium chloride solution. The concentration of antipsoriatic agent in the parenteral compositions will normally be from about 1 mg/ml to 50 mg/ml, and the dosage per treatment will be from 0.5 to 5.0 mg/kg body weight.

For topical application the SnPP or SnMP can be provided in the form of gels, lotions, oils, creams and the like and may contain thickening agents, surfactants, coloring agents, buffers, humectants or other components normally used in such compositions. These novel compositions may also be made isotonic with a selected solute such as sodium chloride, glucose, sodium tartrate or other selected inorganic or organic solutes.

The topical compositions will typically contain from about 1 to 50 mg/ml of active agent together with a pharmaceutically acceptable carrier. They may be utilized by application to the affected area with a gauze pad, as an aerosol spray or other selected mode.

Treatment with SnPP or SnMP is utilized together with exposure to ultraviolet light. The exposure may be to ultraviolet light itself, sunlight or any artificial light which includes light in the ultraviolet region of the spectrum. Exposure may take place simultaneously with the administration of the therapeutic agent or subsequent thereto, and will be effective so long as unmetabolized SnPP or SnMP remains in systemic distribution. To be most effective the total dose of ultraviolet energy to which the patient is exposed should be at least 2.5 joules/cm$^2$. There is no particular upper limit to the dose, but it should remain below the level at which exposure to ultraviolet radiation becomes toxic which is normally about 60 joules/cm$^2$.

The following non-limiting examples are given by way of illustration only.

EXAMPLE 1

This example illustrates typical ointments for use in this invention.

| A | |
|---|---|
| Boric Acid NF | 1.740 g |
| Methylcellulose (4000 CPS) USP | 2.000 g |
| Acetic Acid NF | 0.100 g |
| Sodium Acetate (Anhydrous) USP | 0.270 g |
| Glycerin USP | 5.000 ml |
| SnPP | 0.100 g |
| Water, Purified USP q.s. | 100.000 ml |
| B | |
| Potassium Chloride USP | 1.080 g |
| Hydroxyethyl Cellulose | 1.000 g |

| | | |
|---|---|---|
| (3500-4000 CPS) NF | | |
| Acetic Acid NF | 0.100 | g |
| Sodium Acetate (Anhydrous) USQ | 0.270 | g |
| Propylene Glycol USP | 5.000 | ml |
| SnMP | 0.050 | g |
| Water, Purified USP q.s. | 100.000 | ml |
| C | | |
| Dextrose USP | 5.120 | g |
| Polysorbate 80 USP | 10.000 | g |
| Methylcellulose (4000 CPS) USP | 1.33 | g |
| Acetic Acid NF | 0.100 | g |
| Sodium Acetate (Anhydrous) USP | 0.270 | g |
| Glycerin USP | 5.000 | ml |
| SnPP | 0.015 | g |
| Water Purified USP q.s. | 100.000 | ml |
| D | | |
| Propylparaben NF | 0.010 | g |
| Sodium Chloride USP | 0.820 | g |
| Xanthan Gum NF | 2.000 | g |
| Acetic Acid NF | 0.100 | g |
| Sodium Acetate (Anhydrous) USP | 0.270 | g |
| Propylene Glycol USP | 5.000 | g |
| SnMP | 0.200 | g |
| Water, Purified USP q.s. | 100.000 | ml |

EXAMPLE 2

A total of 10.73 mg of SnMP was taken up in 0.2 ml of 5N aqueous sodium hydroxide and 7 ml of 0.9% aqueous sodium chloride was added. The pH was adjusted to 7.4 by the addition of 2N hydrochloric acid. The resulting composition contained 1.073 mg/ml of SnMP.

EXAMPLE 3

The patients in this example were evaluated by subjective evaluation of erythema, scaling, indurator and pruritus according to the following scale. The score given in each case is the total of the four evaluations.

| Score | Interpretation |
|---|---|
| | ERYTHEMA |
| 0 | Normal Skin |
| 0.5 | |
| 1.0 | Mild, comparable with syphilic roseolae |
| 1.5 | |
| 2.0 | Pronounced erythema comparable with pityriasis rosacea |
| 2.5 | |
| 3.0 | Severe, like descaled psoriasis plaque |
| | SCALING: |
| 0 | No scales |
| 0.5 | |
| 1.0 | Mild, powder-like, as in pityriasis rosacea |
| 1.5 | |
| 2.0 | Moderate, like untreated nummular psoriasis |
| 2.5 | |
| 3.0 | Severe, like advanced scalp psoriasis |
| | INDURATION: |
| 0 | Flat on palpation |
| 0.5 | |
| 1.0 | Mild, like induration in nummular excema |
| 1.5 | |
| 2.0 | Moderate elevation, like untreated psoriasis plaque |
| 2.5 | |
| 3.0 | Severe induration, like lichen verrucosis |
| | PRURITUS: |
| 0 | Absence of pruritus |
| 0.5 | |
| 1.0 | Mild itching, no interference with patient's lifestyle |
| 1.5 | |
| 2.0 | Moderate, patient disturbed by itching, may not sleep, physical evidence of excoriations |

| Score | Interpretation |
|---|---|
| 2.5 | |
| 3.0 | Severe, patient's lifestyle disrupted by symptoms |

A

K. M. born 1928 a Swedish male had psoriasis since 1972. He also has psoriasis arthritis. For long periods of times he had been treated as an in patient and also by visiting psoriasis centers 2-3 times a week for UVB, Dithranol treatment. This psoriasis was wide spread and hard to treat. The distribution was about 30-40% of his body, arms, legs, head, back, chest. Prior to the treatment with SnPP he was treated with UVB, Dithranol and tar-baths. The disease had been stable for at least 4 months of unsuccessful treatment prior to entering study. After being given the SnPP injections at a dosage of 2 umol/kg he was treated 4 times a week with UVA starting at 3.5 J/cm$^2$. The dose was raised 1 J/cm$^2$ a week. His plaques were evaluated once a week. The score prior to the study was 9 points. After one week the score was 7 points and after another week the score was 4.5 points. After 4 weeks the score was down to 3 points and, after another 2 weeks, 2 points. Six weeks after the treatment parts of his body were completely clear and other parts were almost completely clear.

The UVA doses given in this case were 3.5 J/cm$^2$ to start with, and at the end of the study 12 J/cm$^2$. Prior to the study he had failed to respond to PUVA in doses much higher than these utilized in the actual study.

B

J.J. a female born in 1937 on Trinidad and resident in Sweden since 1983 has a light brown complexion. Her psoriasis started in 1960. It has been wide spread and distributed to most parts of the body, arms, legs, back, chest and head. Her disease has often been hard to treat. She had earlier been treated with local steroids, tar, UVB, PUVA, and Methorexate. The only real effective modality in her case was Methotrexate. Prior to this study she had been treated for 2 months with Dithranol and UVB without success.

The patient was given SnPP injections at a dosage level of 2 umol/kg and was treated 3-4 times a week with UVA, starting at 8 J/cm$^2$ followed by 4 treatments with 10 J/cm$^2$, 2 treatments with 11.5 J/cm$^2$, 2 treatments with 13 J/cm$^2$. Due to Christmas holiday there was one week without UVA treatment. Each week she was monitored and her plaques were evaluated. Before the treatment she scored 8 points. After one week the score was 6 points and, after another week the score was 5 points. For another two weeks after completion of the treatment the disease was stable, but by the end of the fourth week after the treatment the evaluation had returned to the original score of 8.

EXAMPLE 4

Ten patients with the plaque type of psoriasis, eight men and two women, participated in the study. The clinical data on the patients is presented in Table I. All of the patients had been on continuous treatment for their disease, but for the period two weeks prior to entrance into the study, only emollient local treatment was given. Prior to participation in the study, the patients underwent extensive clinical and biochemical tests all of which were normal. The tests were repeated after the conclusion of the study with similar results.

The study was designed to last three weeks. Sn-protoporphyrin was injected at a dose of 1 umol/kg body weight; a second identical infusion was administered eight hours later. Prior to administration of Sn-protoporphyrin and for a period of 2-4 days after the infusions of the metalloporphyrin UVA-threshold values were measured using a Waldmann UVA 800 unit (Waldmann, Schwenningen, FRG). The back of the patient was illuminated through a green cloth with standaridized square portions (5×5 cm) deleted from the cloth. A positive minimal erythematous reaction was considered to be present when three or more corners of the illuminated square were visible when contrasted to the protected skin portions. After Sn-protoporphyrin treatment, the body of the patient was, while in a standing position, exposed to UVA light 4-5 times a week for three weeks using a Waldmann UV 1000 cabin equipped with 26 UVA lamps. The output of the lamps was measured weekly using a Waldmann meter type 585 100. Suberythematous doses of UVA were given throughout the study with increments of 2 joules per cm$^2$ per week. The degree of erythema, scaling and infiltration in each patient was evaluated prior to Sn-protoporphyrin administration and once weekly during the three week treatment period. The physical examinations of each patient were performed by the same dermatologist and, on each occasion, erythema, scaling and induration were graded on a score of 0.3 using the scales described above.

Treatment with Sn-protoporphyrin resulted in a lowering of the UVA-light thresholds in all patients (Table II). The combination of UVA-light treatment with the metalloporphyrin treatment produced a positive response in all the patients. As is outlined in Table III, there was improvement in the psoriatic lesions in all of the patients treated. In some patients the effect was dramatic with the disappearance of more than 90% of the lesions. Improvement was observed in several patients one week after the administration of Sn-protoporphyrin. No side effects were observed. The artificially induced light sensitivity produced by Sn-protoporphyrin administration resulted in a slight increase in erythemal and tanning reaction on exposure to sunlight in most of the patients. This effect lasted for up to two months, but did not, however, lead to any discomfort. The present study clearly shows that the administration of Sn-protoporphyrin when combined with suberythematous doses of UVA improved the psoriatic lesions in all ten patients studied, and in some patients the improvement was dramatic.

TABLE I

Clinical data of the participating psoriatic patients (n = 10)

| Patient | Age | Sex | Age of onset | Psoriasis type | Earlier treatment modalities | Response to Previous treatments | Treatment just prior to the study | Disease % of body area |
|---|---|---|---|---|---|---|---|---|
| HM | 58 | M | 27 | Plaque | Local steroids, PUVA Dithranol, UVB, etretinate | IR | PUVA | 20% |
| JJ | 49 | F | 23 | Plaque | PUVA, Tar, local steroids, Methotrexate, UVB | NR | UVB, Dithranol | 20% |
| AM | 34 | M | 32 | Plaque | Local steroids, Dithranol UVB | IR | UVB, Dithranol | 10% |
| LH | 41 | M | 26 | Plaque | Local steroids, UVB, Dithranol | IR | Local steroids | <5% |
| VZ | 55 | M | 52 | Plaque | Local steroids | R | Local steroids | <5% |
| BC | 62 | M | Not known | Plaque | Local steroids, PUVA, UVB | IR | PUVA | 20% |
| SK | 61 | F | 37 | Plaque, pustular | Local steroids, Tar | IR | Local steroids | <10% |
| KK | 49 | M | 36 | Plaque | Local steroids, Grenz rays | NR | Local steroids | <5% |
| GT | 63 | M | 60 | Plaque | Local steroids, Dithranol | NR | Dithranol | 5% |
| KE | 60 | M | 55 | Plaque | PUVA, local steroids, Etretinate | NR | Local steroids | 30% |

\* The response to the actual treatment performed just prior to entering the study.
R = responsive, NR = nonresponsive and IR = intermediate response.

TABLE II

Minimal erythemal reactions (MED) following exposures to UVA-light prior to and after injections of Sn—protoporphyrin, akin types and UVA doses given during the study

| Patients | HM | JJ | AM | LH | VZ | BC | SK | KK | GT | KE |
|---|---|---|---|---|---|---|---|---|---|---|
| MED prior (J/cm$^2$) | <25 | <25 | <25 | <25 | <25 | <25 | <25 | <25 | <25 | <25 |
| MED after (J/cm$^2$) (2-4d) | 10 | 15 | 15 | 10 | 10 | 15 | 5 | 10 | 10 | 10 |
| Skin type | II | V | III | II | II | II | III | III | III | III |
| Starting UVA dose (J/cm$^2$) | 3.5 | 8 | 10 | 5 | 5 | 5 | 2.5 | 6 | 5 | 5 |
| Total UVA dose (J/cm$^2$) (21d) | 62 | 138 | 135 | 115 | 110 | 128 | 26 | 98 | 92 | 78 |
| Number of UVA-treatments | 13 | 12 | 14 | 13 | 12 | 14 | 10 | 13 | 13 | 13 |

TABLE III

The clinical scoring of psoriatic plaques according to the degree of erythema (0-3), scaling (0-3) and induration (0-3)

| Patient | Day 0 | Day 7 | Day 14 | Day 21 |
|---|---|---|---|---|
| HM | 9 | 7 | 4 | 4 |
| JJ | 8 | 6 | 5 | 5 |
| AM | 8 | 7 | 7 | 7 |
| LH | 8 | ND | 4 | 4 |
| VZ | 7 | 3 | 2 | 2 |
| BC | 6 | 4 | 4 | 3 |
| SK | 9 | 5 | 3 | 4 |
| KK | 8 | 7 | 5 | 0 |
| GT | 8 | 6 | 4 | 3 |
| KE | 8 | 9 | 5 | ND |

ND —not done

We claim:
1. A method for treating psoriasis in a human patient in need of such treatment which comprises administer- ing to the patient an antipsoriatic amount of tin protoporphyrin or tin mesoporphyrin followed by exposure to ultraviolet light.

2. A method as in claim 1 wherein the tin protoporphyrin or tin mesoporphyrin are administered parenterally.

3. A method as in claim 1 wherein the tin protoporphyrin or tin mesoporphyrin are administered topically.

4. Therapeutic compositions for topical use containing from 1 to 50 mg/ml of tin protoporphyrin or tin mesoporphyrin together with a pharmaceutically acceptable topical carrier in the form of an ointment, cream, lotion or gel.

* * * * *